United States Patent
Voss et al.

(10) Patent No.: US 9,068,955 B2
(45) Date of Patent: Jun. 30, 2015

(54) POSITIONING DEVICE FOR A LABORATORY APPARATUS FOR THE DISTRIBUTION OF FLUID SAMPLES, LABORATORY ATTARATUS WITH A POSITIONING DEVICE AND POSITIONING METHOD

(75) Inventors: Simon Voss, Hamburg (DE); Holger Link, Hamburg (DE)

(73) Assignee: Eppendorf, AG, Hamburg, DE (US)

( * ) Notice: Subject to any disclaimer, the term of this patent is extended or adjusted under 35 U.S.C. 154(b) by 0 days.

(21) Appl. No.: 13/558,281

(22) Filed: Jul. 25, 2012

(65) Prior Publication Data
US 2013/0047751 A1   Feb. 28, 2013

Related U.S. Application Data

(60) Provisional application No. 61/511,594, filed on Jul. 26, 2011.

(30) Foreign Application Priority Data

Jul. 26, 2011   (DE) .......................... 10 2011 108 537

(51) Int. Cl.
  *G01N 35/10*   (2006.01)
  *B01L 9/00*   (2006.01)
  *B01L 3/02*   (2006.01)

(52) U.S. Cl.
  CPC .......... *G01N 35/1011* (2013.01); *B01L 3/0224* (2013.01); *B01L 9/523* (2013.01); *B01L 9/54* (2013.01); *B01L 2200/025* (2013.01); *B01L 2300/0861* (2013.01)

(58) Field of Classification Search
  None
  See application file for complete search history.

(56) References Cited

U.S. PATENT DOCUMENTS

| | | | |
|---|---|---|---|
| 4,235,971 A | | 11/1980 | Howard et al. |
| 4,473,213 A | * | 9/1984 | Decker .......................... 254/8 B |
| 4,478,094 A | | 10/1984 | Salomaa et al. |
| 4,827,780 A | | 5/1989 | Sarrine et al. |
| 5,415,060 A | | 5/1995 | DeStefano, Jr. |
| 5,672,320 A | | 9/1997 | Ritter |
| 6,199,435 B1 | | 3/2001 | Wilmer et al. |
| 7,597,854 B1 | | 10/2009 | Reynolds |

(Continued)

FOREIGN PATENT DOCUMENTS

| | | |
|---|---|---|
| DE | 9218750 | 10/1992 |
| DE | 4437716 | 10/1996 |

(Continued)

*Primary Examiner* — Robert R Raevis
(74) *Attorney, Agent, or Firm* — Arnold & Porter LLP; Todd A. Lorenz

(57) ABSTRACT

The invention relates to a positioning device for a laboratory apparatus for distributing fluid samples comprising: a base member, a first part at which a transport device can be arranged, the first part arranged at the base member for carrying out at least one operation movement, a second part arranged at the base member at which a sample container holder can be arranged, the first and second parts movable relative to one another for carrying out positioning movements and adapted to be arranged in relative positions, a coupling device for coupling the operation and positioning movements, set up such that the relative positions of the first and second parts can be stepwise changed by way of repeatedly performing the operation movement; and to a method for automatically positioning a first part relative to a second part and to a laboratory apparatus comprising such a positioning device.

6 Claims, 9 Drawing Sheets

(56) References Cited

U.S. PATENT DOCUMENTS

| | | |
|---|---|---|
| 7,713,487 B1 | 5/2010 | Locklear et al. |
| 2003/0017083 A1 | 1/2003 | Pobering et al. |
| 2006/0110287 A1 | 5/2006 | Kraemer et al. |
| 2007/0221684 A1 | 9/2007 | Steinbrenner et al. |
| 2009/0095091 A1* | 4/2009 | Smith .................... 73/863.81 |
| 2011/0209564 A1 | 9/2011 | Von Beichmann et al. |
| 2011/0296930 A1* | 12/2011 | Deppermann et al. .......... 73/864 |

FOREIGN PATENT DOCUMENTS

| | | |
|---|---|---|
| DE | 102008010267 | 8/2009 |
| EP | 0138205 B1 | 8/1985 |
| GB | 1456555 | 11/1976 |

* cited by examiner

POSITIONING DEVICE FOR A LABORATORY APPARATUS FOR THE DISTRIBUTION OF FLUID SAMPLES, LABORATORY ATTARATUS WITH A POSITIONING DEVICE AND POSITIONING METHOD

The present invention relates to a positioning device for a laboratory apparatus for the distribution of fluid samples, a laboratory apparatus with a positioning device and a method for positioning.

These laboratory apparatuses are useful for the improvement and more efficient configuration of the processes which tend to be performed largely manually, of distributing one or more samples to a plurality of sample wells. Known devices suitable for a manual distribution of samples include e.g. hand-operated pipettes and dispensers. A pipette is understood to mean a device wherein the sample amount dispensed by the device in one single actuation substantially corresponds to the sample amount aspirated into the device. In the case of a dispenser an aspirated sample amount corresponding to multiple portions is dispensed stepwise. Moreover a differentiation is made between single channel devices and multiple channel devices, single channel devices containing one single dispensing channel only and multiple channel devices containing multiple dispensing channels which in particular allow parallel dispensing /aspirating of the samples. Both types of devices allow manual distribution of samples e.g. to the sample carriers of microtiter plates having e.g. 96 or 384 sample wells.

Examples of hand-operated pipettes include Eppendorf Reference® and Eppendorf Research® of Eppendorf AG; an example of a hand-operated dispenser is Multipette® plus of Eppendorf AG; an example of an electronic pipette is Eppendorf Xplorer® of Eppendorf AG; examples of electronic dispensers are Multipette stream® and Xstream® of Eppendorf AG.

Manually filling the sample wells of a microtiter plate requires for the user to memorize which sample well was filled already and which target sample well follows next. Errors may occur such as omitted filling, wrong filling, or inadvertent multiple filling of one sample well since the filling status of sample wells tends to be hardly recognizable in particular when using liquids poor in contrast and transparent relative to the microtiter plate. Using a positioning device which may e.g. be part of a sample distributing apparatus such as a pipetting apparatus, allows a sample processing throughput in laboratories increased over manual pipetting which is in particular useful for screening processes in microbiology and biochemistry.

An increase of the throughput in sample processing is in particular achieved by fully automatic pipetters with fully automatic sample take-up, target position selecting, and sample dispensing. For selecting a target position these machines to not require any predetermined or preset target positions since a plurality of sensors, motors, suitable electronic controls, and optionally control programs tend to be provided by means of which target position selection is controlled. However, this makes the providing of these machines expensive and tends not to be a suitable solution if a medium volume throughput of sample processing is sought. Examples of these pipetting machines can be found e.g. in EP 0 138 205 B1, U.S. Pat. No. 4,478,094 or DE 10 2004 057 450 A1.

What is desirable for medium-volume throughput of sample processing e.g. in small or medium-sized laboratories is manual distribution of samples supported by machines only. These kinds of apparatuses provide for means for more efficient positioning e.g. of pipettes relative to sample holders.

In U.S. Pat. No. 7,597,854 B1 for example a pipetting apparatus with positioning aids is described wherein a row to be filled of a microtiter plate is covered from above by a slit diaphragm with sample dispensing to the row provided through the diaphragm slit. The diaphragm is attached to a guide track where it can be displaced manually parallel to the microtiter plate up to the target row concerned. Marked stop positions facilitate for the operator the positioning and unloading of the pipettes above the marked target row of the microtiter plate which is again done manually. The marking of the stop positions at the guide track which match the designations of the rows of the microtiter plate facilitates the filling of the sample wells. However if the operator is not sure whether or not the marked row has been filled, filling errors may occur in this apparatus for example if the operator fills the microtiter plate row once again without first shifting the diaphragm to the next target position.

From U.S. Pat. No. 5,415,060 a pipetting apparatus is known in which a movable sample holder for holding a microtiter plate is displaced relative to a fixed support bridge for supporting a manually applied pipette. With the sample holder being in a dispensing position relative to the support bridge, a separate step allows to manually approach a filled pipette to the support bridge against which it is placed and the sample can be filled manually by way of dispensing to the microtiter plate row marked by the support bridge. In another separate step the sample holder is then intended to be manually displaced to the dispensing position following next. This occurs by the user displacing a lever connected with an advance mechanism. Now when the user intends to fill the next row of the microtiter plate he needs to remember or recognize whether the current position was already filled or not, i.e. whether or not the sample holder has already changed positions. Another problem of this apparatus and quite generally in manually filling sample wells is that due to the manual movements of the pipette from the supply container to the target position at a microtiter plate the operator and his state greatly influence the uniformity and reproducibility and thus the error rate of the filling process.

Document DE 10 2008 010 267 A1 describes a pipetting apparatus for manually handling liquids in which manual selection of a target position for the pipette is realized by a grid formation. The grid formation serves for improving precision in positioning pipettes and sample container holder. Again there is the problem that the user must remember or recognize whether the current position was already filled or not, i.e. whether or not the sample holder has already changed positions as he wishes to fill the next position of the pipette above the sample container holder.

The German patent application DE 10 2010 005 722.3 published later discloses another positioning device not comprising the characterizing feature of the present claim 1. Said application in particular shows a positioning device in which a drum mechanism allows stepwise advancing of a stop position until positioning movement is possible up to such position.

It is the object of the present invention to provide an alternative positioning device for a laboratory apparatus for the distribution of fluid samples. In particular is it the object to provide a manually operated laboratory apparatus for the distribution of fluid samples, an improved laboratory apparatus with a positioning device, and an improved method for positioning, all of which offer the required throughput of sample distribution with the error rate equivalent or minimized.

The object is solved by the positioning device according to claim 1, the laboratory apparatus according to claim 16, and the method for positioning according to claim 19. Preferred embodiments are the subjects of the respective subclaims.

The positioning device according to the invention, for a laboratory apparatus for the distribution of fluid samples, in particular for a pipetting apparatus, comprises:

a base member, a first part at which a transport device for transporting a sample can be arranged, the first part being arranged at the base member for carrying out at least one operation movement, a second part arranged at the base member at which a sample container holder can be arranged, the first and second parts being arranged movable relative to one another for carrying out at least one positioning movement and adapted to be arranged in relative positions, a coupling device for coupling the operation movement and the positioning movement, the coupling device being set up such that the relative positions of the first and second parts can be stepwise changed by way of repeated operation movements, one operation movement moving the first and second parts starting out from the n-th relative position to the (n+1)th relative position and another operation movement moving the first and second parts starting out from the (n+1) th relative position to the (n+2)th relative position.

The invention is preferably suitable for supporting the user of a manually operated apparatus in selecting the target position in the current positioning step and preferably suitable to achieve precision in positioning the first and second parts in their relative positions, facilitating the same for the user. The positioning device according to the invention serves to stepwise change the relative positions of the first and second parts with a positioning movement preferably being caused automatically by an operation movement. This operation movement is preferably generated manually by the user. Therefore the positioning device according to the invention offers in particular the advantage of not requiring any additional user activities for selecting the relative positions in the actuation step following next, this occurs automatically. This automatic, stepwise changing of the relative positions avoids the risk in particular in the case of a largely manually operated positioning device for a user to err about the status of a target position of a sample holder such that wrong or omitted filling becomes less probable. The invention may likewise be applied in semi-automatic laboratory apparatuses.

Although the sample to be distributed is preferably liquid, it may show another consistency, e.g. being viscous, gel-like, powdery, solid, or gaseous. A sample is typically a solution of chemical or biochemical substances (e.g. reagents for a polymerase chain reaction, PCR), or a biological or medical liquid (blood, serum, urine, etc.). The sample is usually located in the tip of a pipette or tip/sprayer of a dispenser from which it can be dispensed and into which it can be aspirated.

The operation movement is preferably a manual movement performed by a user. The operation movement preferably comprises at least one vertical component or preferably travels substantially linearly in the vertical direction.

The indication of the direction "vertical" presently relates to the direction parallel to the force of gravity. The positioning device and the laboratory apparatus when arranged as intended possess an unambiguous orientation in which the top surface of a fluid sample arranged at the first and/or second part is horizontal due to gravity. The horizontal preferably corresponds to the planar orientation of a carrier plate of the base member, of a take-up plate of the second part and/or of a sample container plate at the second part.

The operation movement may be a movement of the sample transport device relative to the first part, in particular to a dispensing position of the sample transport device towards or away from a dispensing position from which the sample is dispensed out of the sample transport device to at least one sample container in the sample container holder. The operation movement may furthermore be a movement of the first part or any of its components relative to the base member. Such operation movement preferably occurs in the vertical direction, in particular to suitably change the distance between the sample transport device and the sample container holder. In the dispensing position the distance between the sample transport device and the sample container holder is sufficiently reduced so as to ensure safe dispensing of the desired sample amount to at least one sample container at the sample container holder.

The operation movement may also be supported mechanically, e.g. through the action of an electric motor, in particular a linear stepping motor, by electromagnets, or by another motor, so as to in particular boost by a motor the force which the user must apply ("servo movement"). This offers the advantage that in this semi-automatic embodiment the forces which the user must apply are reduced, allowing ergonomically improved operation.

An operation movement may cause an electric signal to be transmitted or influenced, e.g. if the positioning device comprises electronic means for automatically detecting an operation movement. The coupling device may comprise electric means by means of which the detection of the operation movement effects a coupling movement to cause the positioning movement. These electric means may be adapted to process radio signals, e.g. radio frequency (RF) signals. The transport device may for example comprise an RFID chip, in particular a shielded RFID chip the shield of which is temporarily removed due to the operation movement which can be electrically detected at least as an incident by way of RF radiation. The operation movement may, in particular preferably in this case, be the user's pressing an actuating member, e.g. a pipetting dispenser knob, at the transport device. It is possible and preferred for the operation movement to be one by means of which the sample is dispensed from the transport device to the sample container holder, or else triggered, e.g. by means of electric signal processing.

The first part and the second part of the positioning device are arranged movable relative to one another, preferably at least relative to a linear direction R, which may be the y axis of a Cartesian coordinate system. The direction R is preferably the direction of the linear positioning movement. Preferably the first part is arranged at the base member movable substantially perpendicular to said direction R and preferably the second part is arranged at the base member to be movable along and in particular parallel to said direction R (first preferred embodiment). In this case the positioning movement is substantially a movement of the second part along and in particular parallel to the direction R relative to the base member. It is also possible and preferred for the second part to be arranged at the base member to be substantially immovable along and in particular parallel to said direction R and for the first part to be arranged at the base member to be movable along and in particular parallel to said direction R (second preferred embodiment). In this case the positioning movement is substantially a movement of the first part along and in particular parallel to the direction R relative to the base member. Or else it is possible and preferred for both the first part and the second part to be arranged to be movable along and in particular parallel to the direction R relative to the base member. Preferably the second part comprises a sample container holder and preferably the first part comprises a holding device for holding a transport device.

The positioning movement or positioning movements preferably run in parallel to a plane, in particular a horizontal plane. This is advantageous in particular in conjunction with distributing fluid samples to upwardly open sample containers intended to receive or dispense the samples. This applies in particular to pipetting using pipetting apparatuses. Preferably the positioning movements run parallel to said direction R which in particular lies on this plane and which is preferably a horizontal direction. The positioning movement is preferably set up to run linearly or non-linearly at least in part or entirely, for example along a curve, for example a circular curve. Preferably the direction of the positioning movements is substantially parallel to a horizontal straight line. The positioning movement is also referred to as offset.

Preferably and in particular when used in a non-fully automatic apparatus it is provided for a user to manually move the first part relative to the second part. The first part or a transport device arranged at the first part, in particular a pipette, preferably comprises at least one gripping portion, in particular one or two gripping portions for the user to grip the part and move it relative to the base member.

The positioning device, the coupling device and their components each preferably consist of mechanical means and preferably act mechanically, in particular solely mechanically (fully mechanized), and preferably none of these is operated electrically. The advantage of this is that a fully mechanized positioning device or laboratory apparatus comprising in particular a non-electric positioning device can be realized, its manufacturing and operating costs can be kept down and which offers higher flexibility of use due to its being independent of electric energy sources.

However, it is possible and preferred for the coupling device or at least one of its components to be adapted for electric operation at least in part or to comprise electrically operated components. Furthermore the positioning device may comprise other means which are adapted for electric operation at least in part, for entirely electric operation, or comprising electrically operated components.

The coupling device comprises at least one mechanically acting coupling means for coupling the operation movement and the positioning movement to cause stepwise changes to the relative position. A positioning movement preferably causes changes to the relative position of the first part and the second part by exactly one increment. Said increment is predetermined or can be modified through a shifting device, in particular can it be modified by the user or by electronic programmed mode. Due to the operation movement the first part may travel a first distance that is longer than a second distance of the second part, which corresponds to said increment. In this case the coupling device comprises a transmission device having a transmission ratio (positioning movement/operation movement) of less than 1. Otherwise it is larger than or equals 1.

The coupling device preferably is, or comprises, a transmission device. The transmission device is preferably set up to be mechanical, preferably solely mechanical. It may comprise, or be, a gear transmission, friction gear drive, belt and chain drive, screw mechanism, crank mechanism, cam mechanism, or a generating cam mechanism. Or else the transmission device may comprise other known transmission types for the transmission of forces and movement.

Preferably the at least one coupling means comprises at least one first coupling means which is arranged to be movable relative to the base member and/or the first part and/or the second part, in particular relative to the sample container holder, by means of the operation movement. The at least one coupling means preferably comprises at least one second coupling means which is arranged to be immovable relative to the base member and/or the first part and/or the second part, in particular relative to the sample container holder.

Preferably the first coupling means is arranged at the base member to be movable in a direction K for moving the second part in the direction R by way of interaction with the second coupling means arranged immovably at the second part (in particular in the case of the first preferred embodiment according to the invention). Or else it is possible and preferred for the first coupling means to be arranged at the base member to be movable in a direction K for moving the first part in the direction R by way of interaction with the second coupling means arranged immovably at the first part (in particular in the case of the second preferred embodiment according to the invention). In this way an effective transmission of the movement can be achieved for achieving a positioning movement that can readily be reproduced in increments.

Preferably the direction K of the coupling movement of the at least one first coupling means and the direction R of the positioning movement run substantially parallel to a plane, in particular the x-y plane of a Cartesian coordinate system that is preferably arranged horizontally (when applying as intended the positioning direction in the laboratory apparatus for the distribution of fluid samples according to the invention). Preferably a preferably linear positioning movement is achieved by using a rotary coupling means that rotates about an axis parallel to said plane, and/or by using a translationally movable coupling means, and/or by preferably using a biased, second part. These planar arrangements of the coupling means permit a compact or flat structure. This is in particular advantageous in laboratory apparatuses since a compact structure serves for ergonomics.

Preferably the at least one coupling means comprises a lever member which is preferably arranged for transmitting the operation movement of the first part to the positioning movement of the second part. The lever member is preferably a pawl member. The lever member is preferably arranged pivotally with the pivot axis preferably extending substantially perpendicular to this plane (e.g. the x-y plane or horizontal plane). This allows a compact structure.

Preferably the coupling device is set up such that the operation movement causes a coupling movement of the at least one first coupling means and that said coupling movement mechanically interacts with the second coupling means for changing the relative position by one step of a predetermined increment. This coupling device, in particular a transmission device of the coupling device, may be designed in different configurations. Examples thereof will be described below by way of the FIGS. 1a, 1b, 1c and 1d. In the Figures the dark dot represents the connection of the mechanism of the coupling device to the second part that is presently supported movably. In each of the configurations it is also possible for the first part to be supported movable and the second part, stationary. A "stationary" part is arranged at, or forms part of, the base member.

In the configuration 1 of the inventive positioning device 10 in FIG. 1a the second part 12 can be moved stepwise relative to the stationary first part 11 by way of a coupling device (13, 15, 16). By way of a rope member 13 or two rope members 13, 14 the second part is biased relative to the stationary first part 11 by means of a spring member 15. The offset (=the positioning movement) occurs for example by unwinding the rope member 13 from a drum 16. To this end the rotary mechanism of the drum can be directly coupled with the first part. For realizing different offset increments the mechanism implementing the offset may be configured such that different offset distances can be realized, e.g. by means of a transmission, in particular having a transmission ratio<1. The problem of preventing unintentional changes in position in the positive y direction may be solved by way of the control cable toward the drum. In the negative y direction the second part can deflect since only the spring retains it in position. The mechanism for releasing the offset is preferably adapted to allow the user to freely choose positions of the second part. A mechanism fulfilling the functions indicated above requires very weak operating forces for offset since the potential energy is already stored in the spring member.

In the configuration 2 of the inventive positioning device 20 in FIG. 1b the offset of the second part 22 over the stationary first part 21 is effected via a rotary part of the coupling device 23 whose rotational axis lies in parallel to the x-y plane. The present rotary part is the spindle member 23. A spindle nut is preferably connected with the second part. To enable shifting between different offset increments, another transmission device may be provided for coupling with the first part. Depending on the spindle pitch a self-locking spindle nut may be used to prevent unintentional position changes. In the case of a steep spindle pitch the spindle member may be secured against twisting by an additional mechanism. The effect of a preferably provided device for manual position selection of the relative position is also related to the spindle pitch. Either the operator can rotate the spindle member or the second part can be readily displaced in the y direction after releasing the rotation lock. This principle solution allows excellent implementation in particular when using an electric motor. Manual actuation of the spindle member can be achieved via a rope member arranged for stepwise rotation of the spindle member.

In the configuration 3 of the inventive positioning device 30 in FIG. 1c the second part 32 is offset relative to the stationary first part 31 via the back and forth movement of a lever member 33 of the coupling device (33, 34) namely, by the pawl member 33 which is in particular used as a ratchet member. Due to the bias of the spring member 35 e.g. in the positive y direction the pawl member locks into the teeth preferably of a tooth rack member 34 fastened to the second part. To generate the desired increment the pawl member may be guided via a shifting member 36, e.g. a panel member so as to precisely snap into the correct position. For shifting between desired increments the shifting member would have to be displaced by the respective distance. While the pawl member is snapped in the tooth rack member this mechanism is self-locking in the negative y direction. With the pawl member being located above the shifting member there is no positioning safeguard though. To prevent unintentional position changes the mechanism can therefore be extended by a second partial safeguard. For manually selecting a position the pawl member may be pulled onto the shifting member and the second partial safeguard may be released. It should be taken into account that as the pawl member snaps back into the tooth rack member it may generate a minor offset depending on the pitch of the teeth. This principle solution offers the advantage that the pawl member can basically be pulled over the shifting member as far as desired so as to allow ease of coupling with the first part.

In the configuration 4 of the inventive positioning device 40 in FIG. 1d 42 the offset of the second part 42 over the stationary first part 41 is caused by way of the back and forth movement of a lever member 43 of the coupling device (43, 44) namely, by the pawl member 43 arranged pivotally in the x-y plane and in particular arranged at a carriage member 46. Preferably the at least one coupling means 43 comprises a carriage member movable relative to the at least one second coupling means 44 and preferably a guiding device by means of which the carriage member can perform a directed coupling movement K with the direction K of said coupling movement preferably running substantially linearly and perpendicularly to the positioning movement in the direction R. The guiding device is arranged preferably immovable relative to the first part (or to the second part) and is in particular fastened to the base member. The direction K comprises at least one element perpendicular to the direction R of the positioning movement with K preferably extending substantially perpendicular to R. The directions K and R preferably lie in a preferably horizontal plane.

The carriage member preferably comprises a pawl member one of the ends of which is pivotally supported at the carriage member such that the pawl member can be pivoted from a first position to a second position. In the first position of the pawl member the pawl member is preferably deflected by an angle of rotation a relative to the direction of the coupling movement K and is furthermore preferably prohibited from pivoting further by means of being stopped in a stop area (stop position). The stop area may preferably be positioned variably by means of a shifting device to realize different increments. In the second position of the pawl member the pawl member is aligned substantially parallel to said direction K.

During the coupling movement the pawl member engages between the recesses of an arrangement, in particular an in-line arrangement preferably comprising the projection members.

Preferably the second part is provided with a sample container holder comprising a top surface for carrying at least one sample container member and a bottom surface with the at least one second coupling means comprising an in-line arrangement of projection members 44 arranged spaced apart and parallel to the direction of the positioning movement, which serve as stoppers in contacts with the contact portion of the pawl member.

The projection members of the arrangement are preferably arranged spaced apart in particular equidistantly, and parallel to the direction of the positioning movement. The distance between pairs of projection members is preferably selected so as to correspond to the desired increment which is preferably determined by the angle of rotation α. The two projection members may be adjacent or separated by at least one other projection member.

The projection members preferably serve as stoppers in contacts with the contact portion of the pawl member. The in-line arrangement is preferably a pin arrangement. A projection member is preferably formed by a pin member 44 that is preferably cylindrical. The carriage member can be moved in the direction K preferably by means of a guiding device.

Preferably the carriage member comprises a spring member clamped between the carriage member and the pawl member so as to cause a restoring force, preferably as the pawl member is pivoted from said first position to said second position.

Preferably the pawl member comprises a contact portion which serves to transmit a force from the carriage member to the second part by way of the contact portion moving the second part during a coupling movement by way of a gliding contact with the at least one second coupling means by precisely one increment, in the positioning movement direction.

In the case of movement in the direction K in the negative x direction (FIG. 1d: "to the right") the pawl member flips to the side and in the case of movement to the left a projection member glides along the contact area of the pawl member. In this way the second part is displaced by one increment in the positive y direction ("forwardly").

To allow different increments the angle of rotation a of the pawl member can be changed. A shifting device may serve therefor. Preferably the coupling device comprises a shifting device for specifying the increment of a positioning movement with the shifting device preferably comprising a contact piece movably supported at the carriage member at which the stopper area is preferably arranged.

To prevent unintentional position changes the carriage member may be provided with a safety device. The coupling device, in particular the safety device, preferably comprises at least one securing means for at least partially fixing the relative positions of the first and second parts. The safety device may comprise at least one accommodation for receiving a coupling means, in particular a projection member. The safety device may be a locking pin which is pushed between the pins due to movement of the carriage member. In this way in particular the pin arrangement can be secured until the carriage is moved. For manually selecting a position the coupling device may be set up such that the pins are moved between and through the pawl member and the safety device. The configuration 4 is a simple implementation of a coupling device capable of combining all the required functions in one mechanism. Moreover it allows safe and precise positioning. In this configuration 4 the operation movement generates a back and forth movement of the carriage member.

Reference is again made below to the coupling device independently of the preferred configuration: Generally the coupling device preferably comprises a third coupling member. It may be a transmission member for transmitting the operation movement B to the coupling movement K. The transmission member may be a gear transmission member. The transmission member is preferably a pulling member, in particular a rope member, for transmitting the operation movement to a first coupling means. Preferably the positioning device is provided with at least one reversing means for reversing the puffing direction of the rope member.

The positioning device preferably comprises a guiding device by means of which a guided operation movement of the first part can be carried out relative to the base member between a start position and an end position. An end position preferably comprises the option for the sample to be dispensed from the transport device to the sample container holder in the end position (dispensing position). Preferably the positioning device comprises the height adjusting device. The positioning device further preferably comprises the springing means for cushioning the operation movement prior to arriving at the start and/or end position.

The positioning device further preferably comprises a guiding device by means of which to perform a guided positioning movement of the first part relative to the second part, in particular a guided positioning movement of the second part relative to the base member or of the first part relative to the base member. A guiding device may comprise one or more, preferably two, guide rods or guide tracks preferably extending in the direction of the operation movement, or in the direction R of the positioning movement. A guide track may comprise a track which in perpendicular cross-section is T-shaped, L-shaped, U-shaped or I-shaped, or in some other design, which may be fixedly arranged at the first or the second part. One or more guided members may be substantially fixedly connected with the second or the first part to be guided during a positioning movement. A guided member may be arranged so as to surround a guide track in part form-closed, having adequate play for friction-less gliding. The direction of guiding is preferably linear so as to allow a linearly translational guiding movement (operation movement or positioning movement).

The base member may comprise a carrier plate arranged preferably horizontally, and may further comprise a rack and/or a housing or housing portions to in particular surround the positioning device at least in part. The base member is preferably set up for carrying the other components of the positioning device and/or the laboratory apparatus. The base member is preferably set up to be adequately compact so as to allow its being placed on a laboratory worktop (work bench) or a laboratory work table.

The first part and/or the second part preferably each comprise at least one carriage member that can be moved by being guided by a guiding device. The first part preferably comprises a third part which may be, or comprise, a carriage member movable in the horizontal direction (e.g. x direction), also referred to as an x carriage. The first part furthermore preferably comprises a fourth part which may be, or comprise, a carriage member movable in the vertical direction (e.g. z direction), also referred to as a z carriage. The x carriage and the z carriage may be part of the height adjusting device.

The positioning device according to the invention provides for the first and the second parts to be movable relative to one another and stepwise in series to a plurality of N relative positions so as to allow to distribute e.g. samples in a plurality of relative positions. N is a natural number larger than one and preferably between 2 and 96, particularly preferably 2, 3, 4, 6, 8, 12, 16, 24, 32, 48, 64, 96, or else larger than 96, e.g. up to 384 or 1536. The number preferably corresponds to the number of sample containers arranged in series, for example the number of rows of a sample plate, in particular microtiter plate.

The coupling device is preferably set up for preferably translational displacement of the relative positions relative to one another by a predetermined increment, as a minimum n times, in particular the first and second parts at least n times. The number n preferably corresponds to the number of rows of a sample container plate which can be arranged at the second part and to which fluid samples are intended to be dispensed, and in particular corresponds to the number N. When a sample container plate having 12 rows of sample containers is used, then preferably n=12, so as to allow selecting and filling each of the rows of said sample container plate. This may in particular apply to standard 96-well microtiter plates.

The increment preferably corresponds to the distance of the centers of sample container elements in the horizontal plane (e.g. x-y plane), which may be, or are, arranged at the second part. For a standard microtiter plate having 96 depressions ("wells"; cf. ANSI/SBS 4-2004) the distance is preferably 9 mm, for a 384-well microtiter plate, preferably 4.5 mm. Other increments may be chosen e.g. depending on the arrangement of the sample containers or type of the sample container element.

The predetermined relative positions are preferably substantially predetermined by the positioning device structure and they may be in particular selected in dependence on a specific distribution pattern desired e.g. corresponding to the distances of sample containers in a sample container holder, e.g. the distances of the rows of sample wells (wells) in an (e.g. standard) microtiter plate ("well plate").

Or else it is also possible and preferably provided to allow choosing or adapting the predetermined relative positions per se for example by way of the positioning device having means for adapting increments, in particular the shifting device. This allows still greater flexibility in using the positioning device so as to distribute e.g. samples in adapted distribution patterns and distribution distances. In the case of pipetting apparatuses having such a positioning device, e.g. other sample container holders can be used, e.g. other than a 96-well or 384-well microtiter plate, plates showing different numbers of sample wells and different distances between sample wells, in particular also non-standard sample container holders.

It is likewise possible for the number of the relative positions to be substantially not predetermined or limited, e.g. by providing for continually changing the relative positions.

The positioning device, preferably the coupling device, preferably comprises at least one safety device (see above) comprising in particular at least one securing means for fixing the relative position at least in part. The securing means may be a means for blocking the positioning movement in the relative position so as to block relative movability of the first and second parts in the relative position at least in the direction parallel to the positioning movement. The securing means may comprise an arresting mechanism, e.g. a snap-in mechanism.

Preferably the coupling device comprises a shifting device for specifying the increment of one positioning movement. Preferably the shifting device comprises a contact piece movably supported at the carriage member. This shifting device or this contact piece allows in particular to influence the movement of a coupling means of the coupling device for example in that movement of the coupling means can be blocked by the contact piece, specifically in a contact piece position that can be adjusted variably (e.g. by the user, or e.g. by the take-up plate selected by the user which in particular serves as an adapter for the sample container member). Automatic setting of the position by placing the take-up plate offers the advantage that the user does not need to decide which setting to chose, such that another potential error source is avoided.

The positioning device according to the invention is preferably characterized in that it comprises means for manually setting the n-th relative position from a plurality of N predetermined relative positions. This allows not only to adjust by increments a wider relative position than set but also to manually or automatically select relative positions independently of the coupling device. Such manual adjustment means is preferably configured for mechanical or electric drive and may e.g. comprise an adjusting knob with markings for marking the relative positions set and may be connected with the second part or the first part in particular via a transmission and/or a push rod so as to provide for direct displacement of the second part or the first part by means of the adjusting knob.

Preferably the inventive laboratory apparatus comprises a disabling device by means of which to prevent the operation movement causing a positioning movement. The advantage of this is more flexibility in using the laboratory apparatus by allowing to perform the operation movement by means of disabling the coupling so as to not necessarily cause the positioning movement, in particular temporarily or until the coupling device is reactivated. Preferably said disabling device can be operated manually or automatically, e.g. program-controlled. A second operating mode may be provided in which the coupling device is disabled by the disabling device while in the first operating mode it is activated. A user may for example decide by way of said disabling device to first use the laboratory apparatus in the first operating mode and to temporarily switch to second operating mode e.g. to manually modify the filling of a sample container plate filled in first operating mode. The disabling device may comprise a watchdog circuit such that e.g. said first operating mode is the standard mode. The disabling device may be configured so as to prohibit the action of the coupling device during disabled mode in that the disabling device comprises respective mechanical and/or electric or other means. The disabling device may for example comprise a lever which in the case of disabling blocks a coupling means of the coupling device such that there will be no automatic coupling of the operation movement with the positioning movement.

The positioning device according to the invention is preferably characterized in that means for cushioning the relative movement of the first and second parts are provided as the relative movement approaches the n-th relative position. In this way e.g. a violent impact of the first and second parts is prevented so as to prolong the service life of the components and to maintain the precision of the positioning device and prevent e.g. a liquid sample from being dispensed from the transport device in an undesired position due to such impact as the target position is reached. The cushioning means may comprise elastic members, e.g. springs such as coil springs, leaf springs, or elastic buffers e.g. of rubber, or may comprise stop cushioning devices e.g. on a magnetic basis. It should be taken into account that high precision in positioning the first and second parts is imperative and should moreover show long-tem stability such that the cushioning means should be selected accordingly.

The laboratory apparatus according to the invention comprises in particular a positioning device which is in particular configured according to the invention.

The inventive laboratory apparatus may be a pipetting machine, in particular a pipetting robot, a semiautomatic pipetting machine, or a pipetting apparatus adapted for in particular manual operation or actuation, all of which configurations may be preferably provided for automatic, semiautomatic, electrical, partially electrical operation, wholly or partially hydraulic or pneumatic, fully mechanical operation or a combination of mechanical, hydraulic, pneumatic and/or electric operation. The laboratory apparatus is preferably an apparatus for manual actuation to be used in particular without requiring any external electrical energy source. This results in the advantage over a fully automatic electric laboratory apparatus, e.g. a pipetting robot, that mains-independent operation is possible so as to allow more flexibility of operation. Moreover the simpler configuration allows for smaller dimensions and mass of the laboratory apparatus which may be arranged e.g. within a volume of less than 60 cm*50 cm*40 cm or 50 cm*40 cm*30 cm (width*height*depth) or e.g. may comprise a mass of less than 3 kg, 55 kg, 8 kg, 10 kg, 12 kg or 15 kg. A smaller floor area or mass also allows for more flexibility in employing the laboratory apparatus which may thus be placed e.g. on most of the laboratory work tables (work benches) existing and allows easy displacement.

The laboratory apparatus preferably comprises a housing which in particular substantially or at least partially surrounds in particular an inventive positioning device. The housing is preferably connected with the base member. The base member and/or the housing is configured for stationary placement, comprising e.g. rubber feet or the like for a firm stand e.g. on a laboratory workbench. Furthermore a rack may be provided that is preferably connected with the base member and preferably carries at least one component or all of the components of the positioning device. The base member preferably comprises a carrier plate that is in particular arranged horizontally.

The positioning device and the laboratory apparatus and their components are preferably made of metals, e.g. aluminum or steel to achieve the highest precision and long-term stability possible. The positioning device and the laboratory apparatus and their components may preferably also be made of plastics, in particular of high-performance plastics.

Preferably the positioning device and the laboratory apparatus and their components are made of materials ensuring resistance to corrosion, in particular in case that aqueous samples are used, in particular biological media which may be saline. The materials should preferably be chemically inert and substantially without affecting their composition should be fit for treatment with cleaning agents allowing the components to be sterilized e.g. with a 70% alcohol/water mix employed for sterilizing sterile work areas in biological or medical research laboratories. The parts of the positioning device and laboratory apparatus may also be coated to achieve such properties. The surfaces are in particular anodized to provide them with an oxide coating by means of electrolytic methods based in particular on anodic oxidation. This is feasible in particular for aluminum parts.

The laboratory apparatus is preferably configured for use with a conventional transport device, in particular a pipette, in particular multichannel pipette or dispenser. The transport apparatus, in particular the pipette, multichannel pipette or dispenser transfer a tip filled with a sample (pipettes) or sprayer (dispenser) to a target position at a sample container element, in particular a target position at a plate. At the target position the sample is emptied into the sample container receiver of the sample container element. Examples of preferably usable multichannel pipettes are the multichannel pipettes Eppendorf Research®, and Eppendorf Research® plus, for electronic pipettes the pipettes Eppendorf Research® pro and Eppendorf Xplorer® by Eppendorf AG.

The inventive laboratory apparatuses may likewise be used with dispensers such as the dispensers Multipette® and the electronic dispensers Multipette® stream and Multipette® Xstream by Eppendorf AG.

Or else it is possible and preferred for the transport device in particular the pipette to be specifically configured for use with an inventive laboratory apparatus and to be configured for exclusive use and/or incorporation in the laboratory apparatus.

A multiple pipette preferably usable with the inventive laboratory apparatus preferably comprises 2, 4, 6, 16, 24 or particularly preferably 12 or still more preferably, 8 channels. These multiple pipettes are particularly suitable for filling standard microtiter plates or other microtiter plates. An eight-channel pipette may in particular be used for filling 96 well, 384 well, or 1536 well microtiter plates.

Conventional standard microtiter plates or other plates each particularly preferably comprise 96 or 384 sample wells, or preferably 4, 8, 12, 16, 32, 64, 192, 1536, 6144 wells or another number of sample wells. Suitable conventional microtiter plates are e.g. Eppendorf Plate® Polypropylene having 96 or 384 sample wells, or Eppendorf Deepwell Plates® having 96 or 384 sample wells by Eppendorf AG, each independent of the bottom shape. The microtiter plates described are preferably provided for use in the laboratory apparatus if other sample container holders having multiple interconnected sample containers (e.g. sample wells) or for holding single sample containers, e.g. sample tubes, are possible as well. It is in particular also possible to work with adapters which may receive different configurations of sample container holders.

Different types of sample container elements, in particular multiple container elements are known or may be defined to be used with the inventive positioning device or the inventive laboratory apparatus. Preferably a sample container holder is set up to hold at least one sample container element. Concrete examples of sample container element types are Cryo containers, Falcon containers (1.5 ml and 50 ml), glass containers and glass beakers, microtiter plates (MTP), Deep Well Plates (DWP), cell culture plates, slides, and PCR plates having 96 or 384 wells. Compared to "normal" microtiter plates, DWP show greater plate and container heights and have more mass. According to ANSI standard and to recommendations by the Society of Biomolecular Screening (SBS) the dimensions (length×width×height) of microtiter plates are 127.76 mm×85.48 mm×14.35 mm. Relevant standards for these standardized dimensions are e.g. ANSI/SBS 1-2004, ANSI/SBS 2-2004, ANSI/SBS 3-2004 and ANSI/SBS 4-2004. A sample container element defined by any of these standards or another standard is presently referred to as "standard-". Such a type or a standard type may refer to sample container elements having the same structure or may refer to groups of sample container elements which are identical in at least one typical characteristic.

Preferably the laboratory apparatus comprises an arrangement portion for arranging at least one sample container element which may comprise a receiving plate for receiving the sample container element or part thereof. The receiving plate may be configured for receiving one (or more, in particular different) sample container holder(s), or configured to simultaneously or non-simultaneously receive multiple, in particular different, sample container holders. To this end an adapter device and/or a connecting device for connecting with an adapter device may be provided wherein an adapter device, e.g. an adapter frame, allows to hold a specific type of a sample container element, e.g. different types of microtiter plates or integrally interconnected sample containers or else sample containers plugged into each other e.g. in the shape of sample container strips.

Preferably an inventive pipetting apparatus comprises a holding portion configured for holding pipette tips or for holding a pipette tip supply holder. A pipette tip supply holder preferably comprises a rack with a perforated plate in whose holes pipette tips are retained preferably such that an unloaded multichannel pipette can be completely loaded with pipette tips by performing one single, vertical movement. Said holding portion may be configured in a cover plate of the base member and/or housing of the pipetting apparatus, in particular as a recess, and in particular in the receiving plate for receiving at least one sample container element.

The laboratory apparatus according to the invention cannot only be used employing pipettes and dispensers as the transport devices but also used with other transporting or dosing mechanisms for conveying e.g. sample volumes by means of pumps or gravitation.

Preferably the positioning device or the laboratory apparatus comprises a height adjusting device which preferably is, or can be, attached to the first (or second) part or which is separably or inseparably connected by the user with the first (or second) part, and by means of which the height of the first part, in particular of a transport device attached thereat, can be adjusted relative to the second part. This allows to determine in particular at the end of the operation movement an optimal dispensing position or receiving position in the distribution of samples. The height adjusting device preferably comprises a third and preferably also a fourth part which is/are arranged to be movable relative to one another or relative to the first (or second) part. Preferably the height adjusting device comprises a guiding device by means of which the relative movement of the third and—if provided—the fourth part can be guided in the guiding direction, in particular substantially in the z direction, i.e. in the vertical direction. The third and/or fourth parts preferably is/are a holding device for the transport device such as support members.

The height adjusting device may comprise means for cushioning the movement of the third and optionally fourth part(s) to prevent shocks due to the parts hitting the stops and in particular to prevent undesired draining of liquid samples. The cushioning means may comprise elastic members such as springs, in particular coil and leaf springs, buffers of elastic materials such as rubber, or stop cushioning devices based e.g. on magnetic effects. It should be taken into account that preferably, high precision in positioning the third and optionally fourth parts is imperative and should moreover show long-tem stability such that the cushioning means should be selected accordingly.

The stroke of the height adjusting device is preferably dimensioned so as to allow to position the transport device for receiving samples from various suitable kinds of sample supply containers and for dispensing to different kinds of sample container elements. The height adjusting device preferably comprises an adjusting device for selecting predetermined heights. Predetermined heights which may be adapted e.g. to the heights of standard sample plates or to the lengths of standard pipette tips, can thus be directly and easily adjusted by the user requiring no measuring or substantially no extensive checking of heights. Such a stroke can for example be definable between 0.5 and 100 mm, 1 mm and 10 mm, 3 mm and 50 mm, 3 mm and 20 mm, or in particular of 4.5 mm or 9 mm to allow quick adjustment of the third and optionally the fourth part relative to the first part for heading for a 96-well or a 384-well microtiter plate.

The laboratory apparatus in particular comprises a holding device and or a fastener for holding and/or fastening a transport device at the first part, in particular a pipette holder which is preferably connected with the first part and can preferably be separated and connected by the user. Different holding devices may be provided for holding various transport devices, or one single holding device may be provided which may be configured for holding different transport devices. Preferably a connecting device is provided by means of which the holding device can be connected with the first part, in particular pivotally connected.

Preferably the laboratory apparatus comprises an inclining device by means of which said holding device for holding the transport device (or e.g. the transport device itself or another component of the first part, in particular the fourth part) can be arranged at an inclining angle $0°<=\alpha2<=90°$ relative to the vertical direction (z direction) wherein preferably $0°<=\alpha2<=45°$ or $0°<=\alpha2<=10°$ or $0°<=\alpha2<=5°$, $\alpha2$ being measured relative to the vertical direction such that in particular the transport devices can be inclined relative to the first part. Preferably the inclining device is connected with the first part. Inclining allows to dispense a sample other than vertically downwardly. It allows for example a user to dispense a sample by means of a pipette tip to the lateral interior wall of a vessel. This is advantageous in the case of small sample volumes if the sample weight cannot overcome the adhesion of the drop at the pipette tip for defined dropping down.

The inclining device preferably comprises an inclining axis arranged substantially horizontal, e.g. an inclining axis rotatably connecting the third and forth parts. The inclining axis may be realized by way of a metal pin which may e.g. be attached to the first part and may be guided rotationally movable through an opening of the third or fourth part. Preferably the inclining device comprises means for locking the inclined position, e.g. a locking wheel. Furthermore the inclining device preferably comprises means for automatic restoring to the vertical position. In this way e.g. a third part rotatable relative to the first part is automatically restored to the vertical position after being released by the user. The means for automatic restoring may comprise a spring such as a helical tension spring which e.g. pulls the third part back to the vertical position as the user ceases to incline the third part.

Preferably the inclining device comprises a guiding device for guiding the holding device for holding the transport device, in particular the fourth part, along a predetermined track curve from a first position in which the holding device (or the fourth part) comprises a first angle $\alpha1$, to a second position in which the holding device (or the fourth part) comprises a second angle $\alpha2$ (e.g. said inclining angle).

Preferably the laboratory apparatus comprises an automatic height adjusting device in which a height-adjustable component of the apparatus is automatically height-adjusted by way of the operation movement. This component is preferably a height-adjustable sample supply container holder so as to allow to use different sample supply containers with the laboratory apparatus and/or to allow comfortable sample take-up by way of automatically lifting the sample supply container in the direction of the transport device. To this end the laboratory apparatus preferably comprises means for changing the height of the (sample) supply container holder in respect of said first and/or second part, e.g. a (e.g. automatic) lifting apparatus with one or multiple lifting members which may comprise a roller and/or a wedge member.

Preferably the laboratory apparatus or the positioning device comprises an electronic supporting device which may in particular be programmable or programmed, in particular may be programmable by the user via a preferably provided user interface of the laboratory apparatus. Preferably the laboratory apparatus comprises means for automatic recognition of the sample container elements. These means may comprise sensors, e.g. electrical or optical sensors. The sample container elements may comprise information sections which can be read by a sensor at the laboratory apparatus. An information section may contain encoded data about the type of the sample container element, for example by means of a 1D or 2D bar code. The control device may be set up to determine, in dependence on the type of the sample container element and/or the adapter which is arranged at the second part, the increment S necessary depending on the type, in particular by means of the shifting device. The control device may furthermore be set up to set, in dependence on the type of the sample container element and/or the adapter which is arranged at the second part, the type-related related dispensing level of the first part (or of the pipette), or the inclining angle of the inclining device, or the starting position of the first and second parts for starting stepwise dispensing of a fluid sample to several rows of sample containers of a sample container plate.

The method according to the invention for positioning a first part relative to a second part in successive steps each in different relative positions by means of a positioning device, in particular of a positioning device according to the invention, in particular in a laboratory apparatus, in particular in a laboratory apparatus according to the invention, in particular in a pipetting apparatus, comprises the steps:

Performing an operation movement at the first part;
Coupling a positioning movement to said operation movement by means of a coupling device of the positioning device, wherein the positioning movement changes the relative position of the first part and the second part, said operation movement moving the first and the second parts starting out from the n-th relative position to the (n+1)th relative position and another operation movement moving the first and second parts starting out from the (n+1)th relative position to the (n+2)th relative position;

optionally: multiple repetitions of the operation movement and in this way optionally performing stepwise changes of said relative position by means of multiple repetitions of positioning movements.

The definitions of terms and explanations of components and means apply to all the subject matter according to the invention, i.e. the positioning device, the sample distributing apparatus and the method, unless a different description is given or the context indicates otherwise. Features of the subject matter and embodiments according to the invention may be combined where it appears feasible or advantageous.

Further preferred embodiments of the positioning device according to the invention, the sample distributing apparatus according to the invention and the method according to the invention can be taken from the following description of the exemplary embodiments in conjunction with the figures and the description thereof. Identical components of the exemplary embodiments are substantially designated by the same reference numerals, unless a different description is given or the context indicates otherwise. The figures show in:

Figure 6:
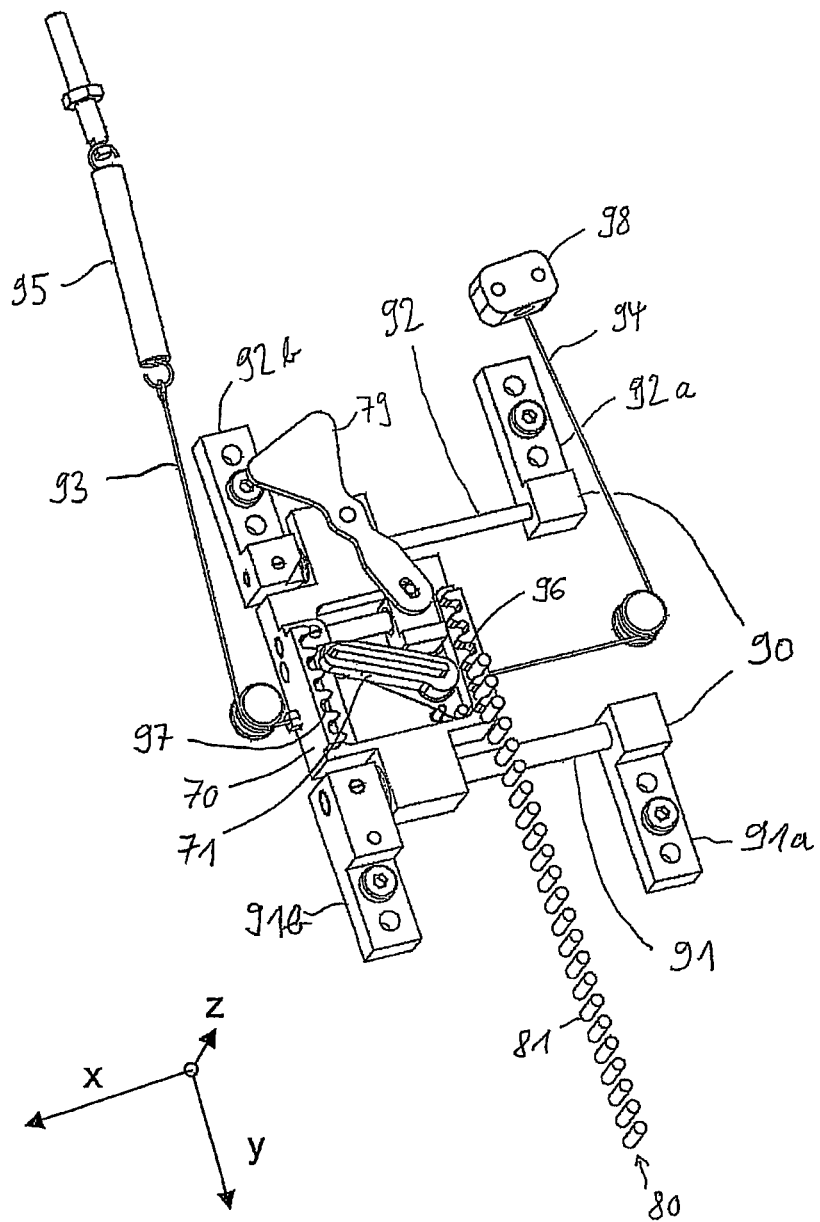
FIG. 6 shows in particular the coupling device of the positioning device according to the FIGS. 3 and 4.
Figure 7:
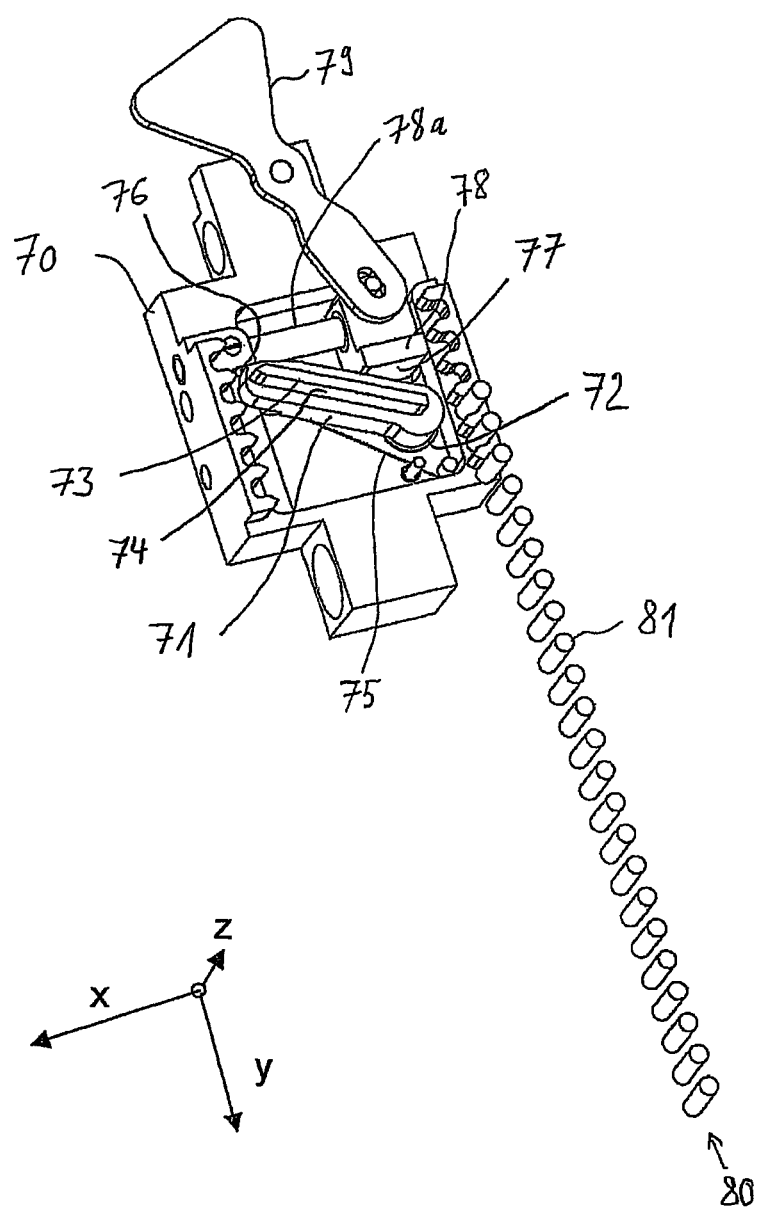
FIG. 7 shows components of the coupling device of FIG. 6.
Figure 8:
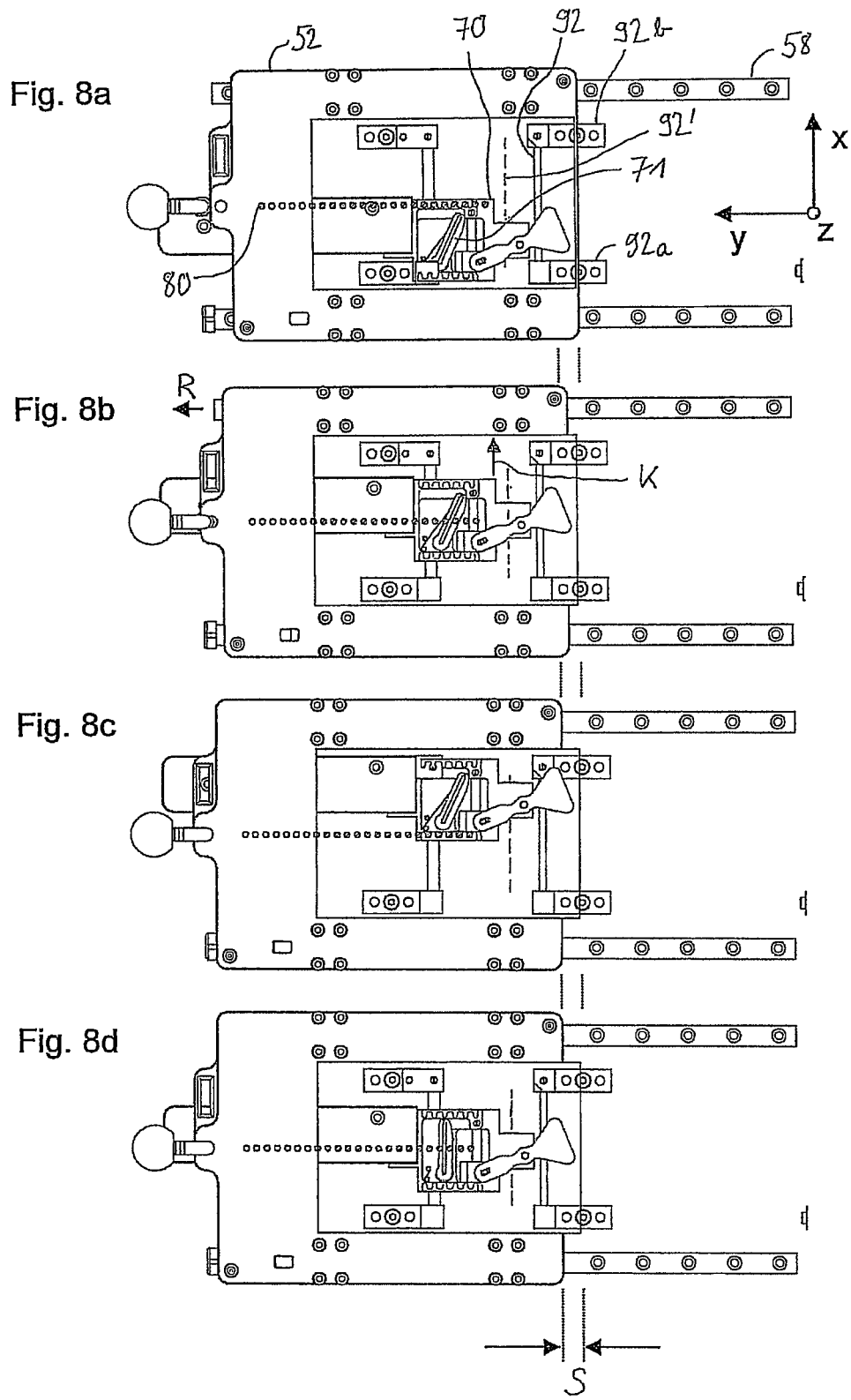

FIG. 8a, FIG. 8b, FIG. 8c and FIG. 8d each show a top view of a different position of the mechanism of the coupling device of FIG. 6 and FIG. 7 and illustrate an example of the method according to the invention for stepwise positioning, and show in particular a positioning step.

Figure 9:
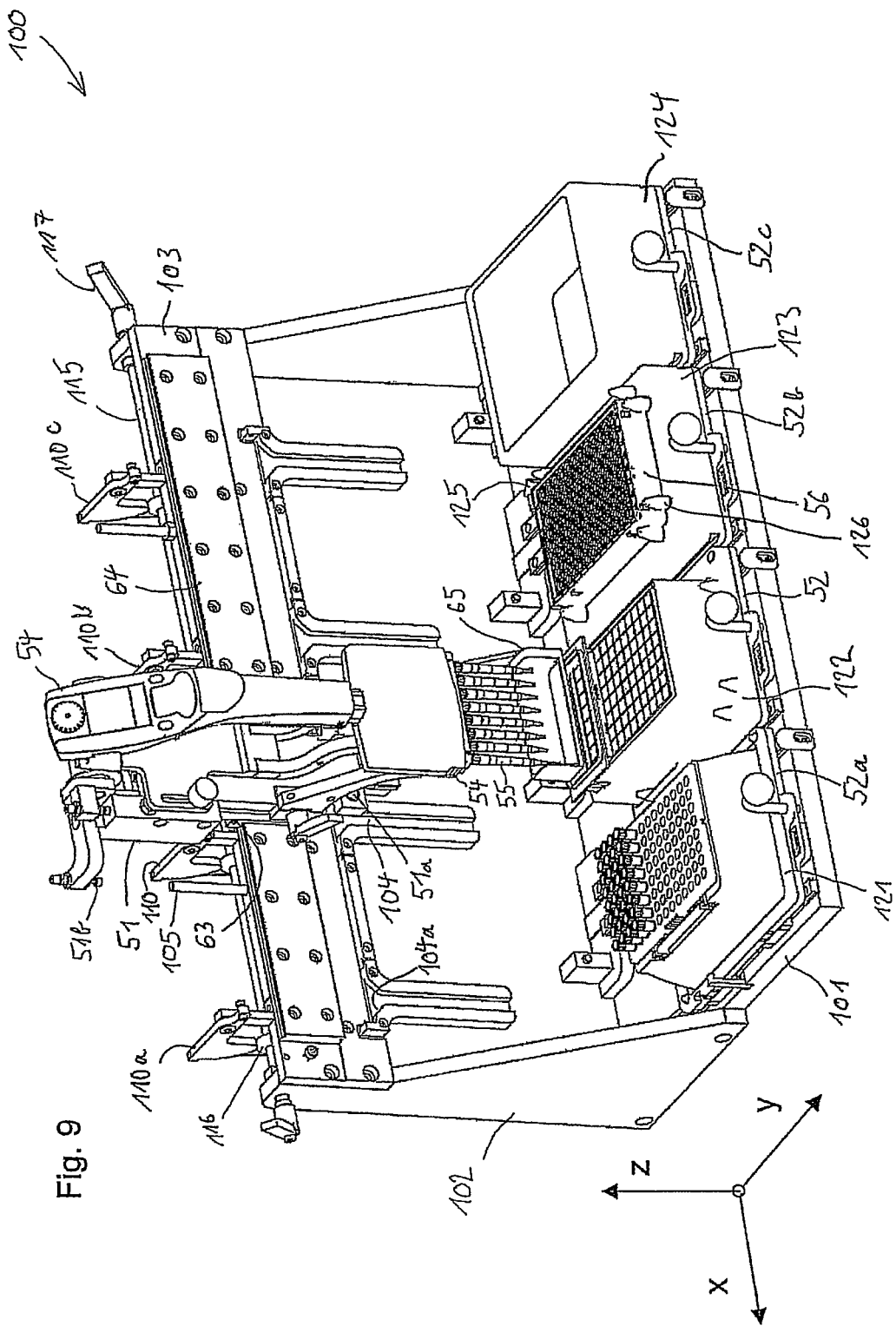

FIG. 9 shows an isometric perspective view of an exemplary embodiment of a laboratory apparatus according to the invention for the distribution of fluid samples by means of the positioning device of FIGS. 3 to 8d, said laboratory apparatus comprising a first part and four second parts.

Figure 2:
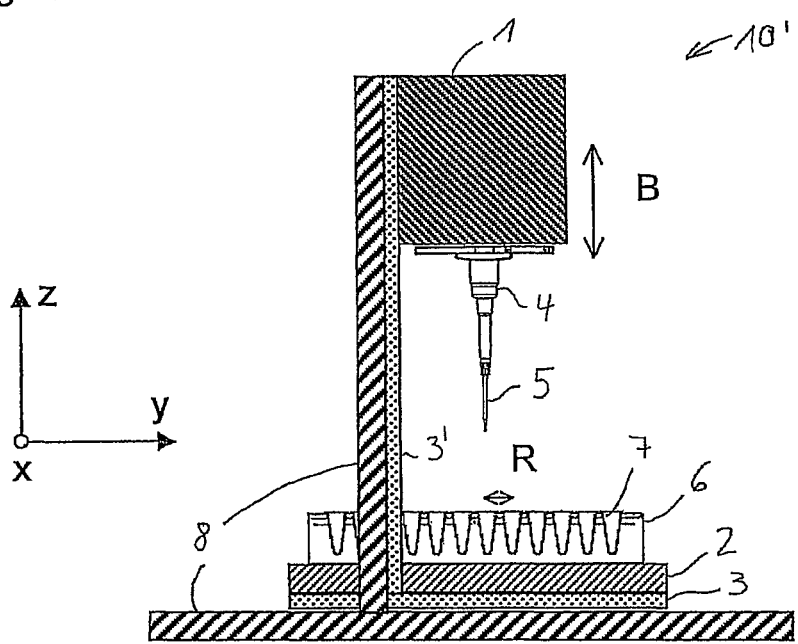
FIG. 2 shows another exemplary embodiment of the positioning device according to the invention.

The positioning device 10' in FIG. 2 serves for stepwise distribution of a fluid laboratory sample to a plurality of sample containers arranged in a microtiter plate. The microtiter plate is retained on the receiving plate 2 of the second part 2. The fluid laboratory sample is provided in a transport device namely, in the pipette tip 5 of the pipette 4. The pipette is fastened to the first part 1. A substantially vertical operation movement B of the first part can be performed by a user. The coupling device (3; 3') is set up such that by way of the operation movement the first and second parts are automatically displaced relative to one another by one increment in the horizontal direction R along the y axis to assume a new relative position. The coupling device comprises coupling means 3 arranged to save space substantially parallel to the horizontal x-y plane. By means of another coupling means which is a transfer member 3', in particular a control cable, the operation movement is transferred to the positioning movement, preferably at a transmission ratio of less than 1. In a relative position the pipette tip is located perpendicular above a sample container 6 of the microtiter plate 6 such that the fluid sample can be precisely dispensed into the sample container. The positioning movement may be caused by the operation movement by way of the first part being moved downwardly (in the direction of the negative z axis). Or else it may be caused by the operation movement as the first part is moved upwardly which preferably occurs by the restoring force of a spring member that had been biased downwardly due to the operation movement. Preferably the first part is arranged at the base member 8 substantially immovably relative to the direction R and the second part is arranged at the base member movable relative to R, corresponding to the first preferred embodiment of the positioning device.

The positioning device according to the invention allows the user to focus on a simple operation movement namely, downwardly movement of the first part 1. In the dispensing position as the pipette is located immediately above a sample container or partially inside a sample container, the user transfers the fluid sample as customary into the sample container by means of the pipette. The user is relieved since he does not need to remember in which row of sample containers in the microtiter plate a fluid sample is already present and in which row, not yet. This is in particular advantageous when distributing small sample amounts or transparent samples which are hard to recognize in the microtiter plate.

Figure 1A:
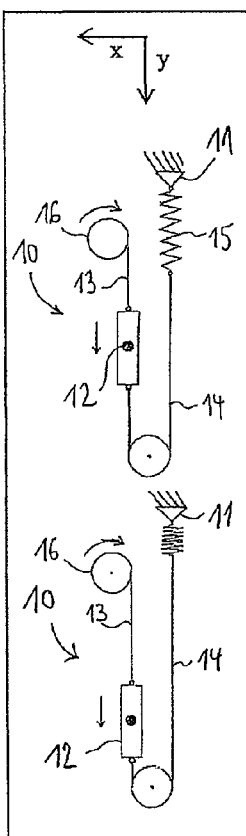
FIG. 1a shows a first exemplary embodiment of the positioning device according to the invention.
Figure 1B:
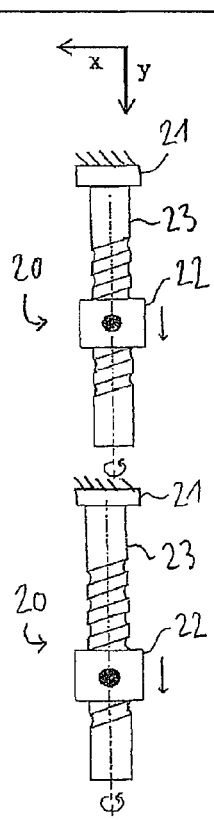
FIG. 1b shows a second exemplary embodiment of the positioning device according to the invention.
Figure 1C:
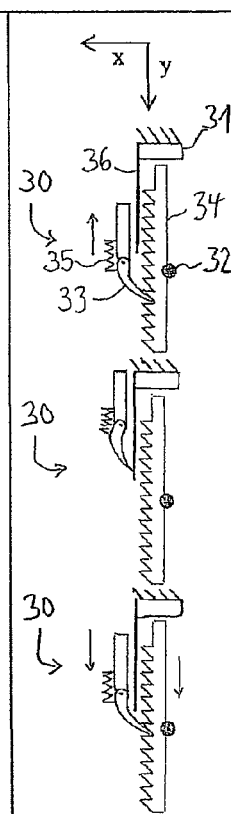
FIG. 1c shows a third exemplary embodiment of the positioning device according to the invention.
Figure 1D:
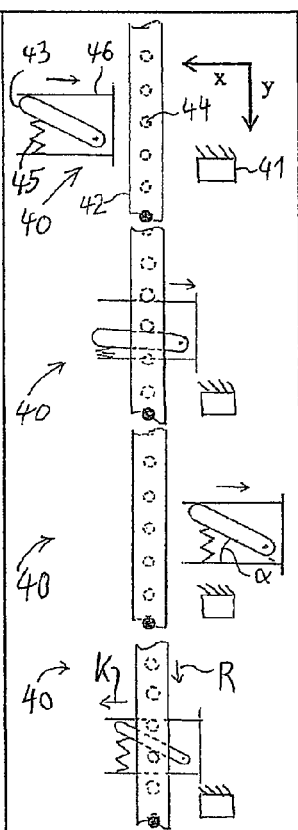
FIG. 1d shows a fourth exemplary embodiment of the positioning device according to the invention.

In the FIGS. 3 to 9 another exemplary embodiment of a positioning device according to the invention and a laboratory apparatus according to the invention comprising this positioning device is described. This exemplary embodiment uses the fourth configuration of the positioning device as explained by way of FIG. 1d. The exemplary embodiment is set up to be used with a commercially available, electronic 8-channel hand pipette Eppendorf Xplorer®, Eppendorf AG, Hamburg, Germany, and in particular with 96 well and 348 well standard microtiter plates.

Figure 3:
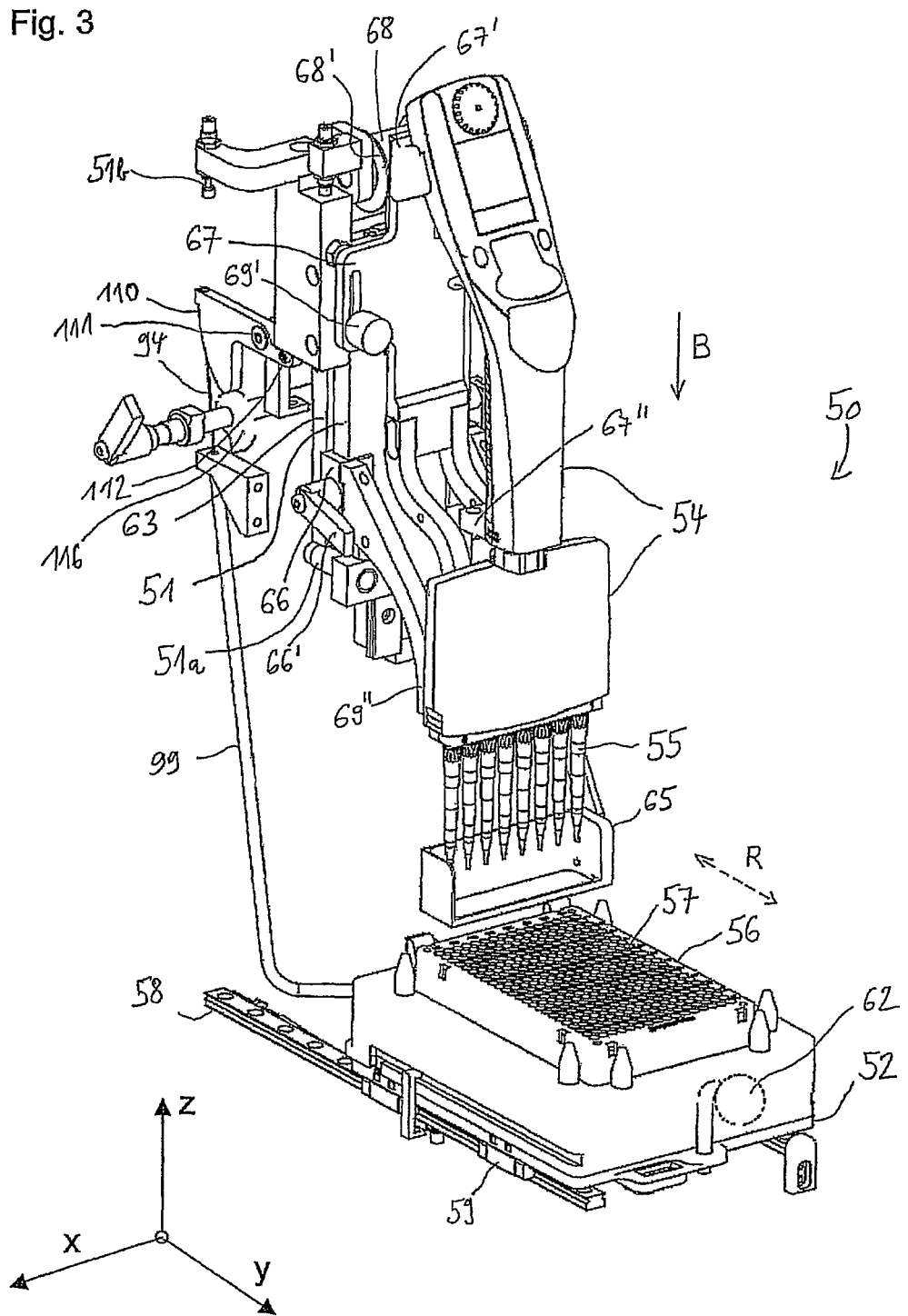
FIG. 3 shows an isometric perspective view of another exemplary embodiment of the positioning device according to the invention, comprising transport device, receiving plate, sample container holder, and microtiter plate.

In FIG. 3 the positioning device 50 is shown. It comprises a first part 51 namely, a carriage member 51 movable in the z-direction (vertically) which can be forcibly moved by means of vertical tracks of a guiding device (not shown). The second part 52 is a carriage member horizontally movable at the base member comprising the receiving plate 52 arranged horizontally (in the x-y plane). The receiving plate comprises at its bottom surface two opposite pairs of bearing members 59 in which the two track members 58 engage and which are supported freely movable on these track members along the y direction. The track members 58 are fixedly mounted to the base member (not shown). The z carriage 51 is not movable in relation to the base member in the y direction.

When processing the 384 well microtiter plate 56 the increment required of the positioning movement R along the y direction is 4.5 mm. Following the first 24 filling steps the plate needs to be displaced 4.5 mm in the x direction or rotated 180° in the horizontal plane respectively. Following another 24 filling steps all of the 384 containers are processed completely. If necessary the second part can be pushed back to the desired position after unlocking.

Now the function of the coupling device will be described by means of which the vertical, downwardly operation movement B of the first part automatically causes the positioning movement of the second part 52 with the microtiter plate by one increment in the direction of the positive y axis. The user causes this stepwise displacement of the microtiter plate comfortably by the simple, vertically guided operation movement of the pipette 54 without having to care about the process of relative positioning of the pipette relative to the microtiter plate. The user guides the pipette tip into the dispensing position in which the pipette tip in 55 enters the sample containers 57 of the microtiter plate 56 a little and as customary dispenses to the microtiter plate the amount of liquid adjusted at the pipette as customary. In this way the positioning device according to the invention allows reproducible and reliable handling of fluid laboratory samples, in particular without involving the risk of cross contamination due to wrong filling.

Figure 5:
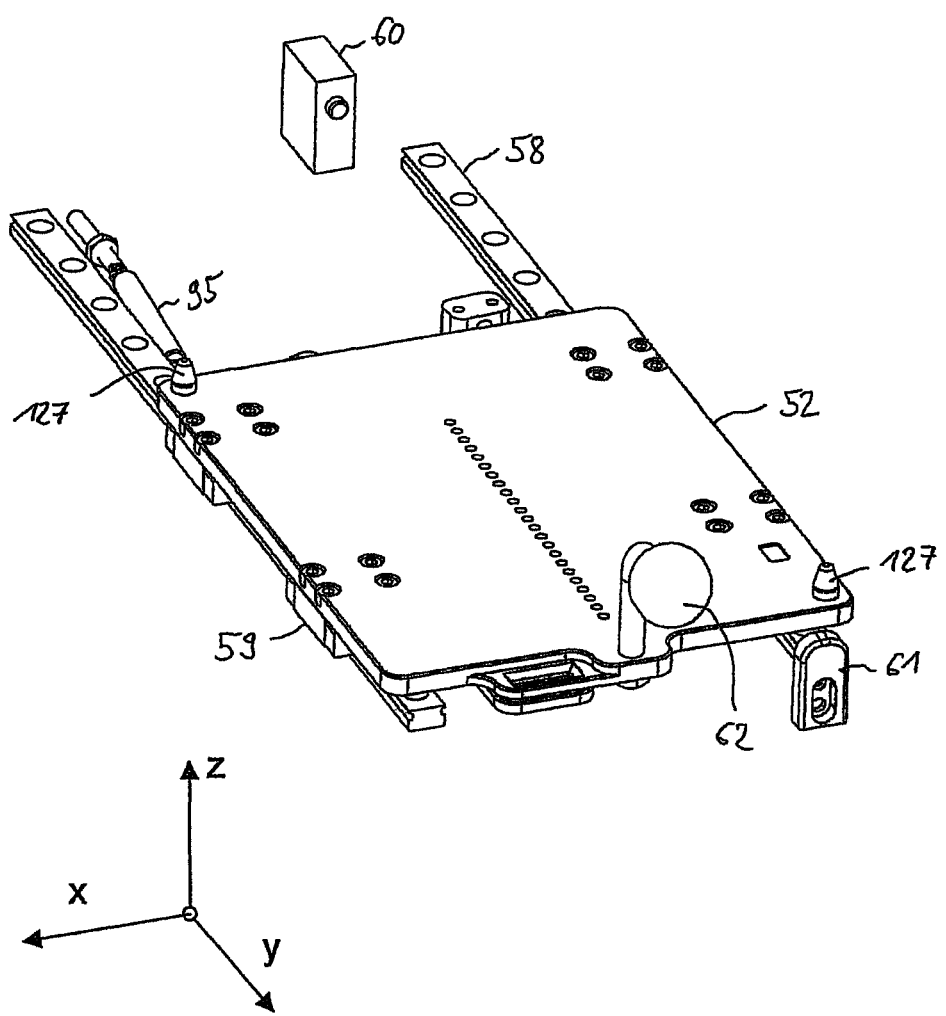
FIG. 5 shows the receiving plate of the second part of the positioning device of FIG. 3 and FIG. 4 comprising the guiding device of the second part.

Displace and lock second part: FIG. 5 shows the second part 52. For reasons of illustration the base member on which the parts are held has been left out. The receiving plate 52 onto which the adapters for the sample container elements are placed is supported via the linear guide 58, 59 in the y direction. The limitation of the guide in the y direction was solved by two stops 60, 61 (see FIG. 5, y guide limitation). When the second part is guided to the rear guide limitation 60, the processing position of the first row of containers or tips has been selected. When the module is guided to the front guide limitation 61, the adapter plates are unlocked and can be exchanged. For optional manual positioning the receiving plate 52 is provided with a grip 62 by which it can be optionally displaced in the non-secured position.

FIG. 7 and FIG. 6 show in particular the first coupling means which by its repeated coupling movement along the x axis displaces the receiving plate 52 in increments. The first coupling means is a carriage member which by means of a guiding device can perform a directed movement along the x axis. The guiding device 90 (see FIG. 6) comprises a first guide rod 91 which are attached to the base member 101 (not shown in FIG. 6) by means of two bearing members 91*a* and 91*b*. It further comprises a second guide rod 92 which are attached to the base member by means of two bearing members 92*a* and 92*b*. The guide rods 91 and 92 extend in parallel to the x axis. The carriage member 70 is also referred to as offset carriage. On the top face of the offset carriage the pawl member 71 is supported in the x-y plane pivotally about the pivot axis in the bearing area 72 of the pawl member. By way of displacing the offset carriage 70 in the direction of the negative x axis ("to the right") the stem-like engagement portion 73 of the pawl member is pushed between the offset pins 81 of the receiving plate 52 by means of the operation movement (not shown in FIG. 7). The offset pins 81 are the projection members of an in-line arrangement 80 of projection members arranged linearly, evenly spaced along the y axis and fixedly (i.e. in particular not removable non-destructively) connected with the bottom surface of the receiving plate 52. Said in-line arrangement is the second coupling means.

The FIGS. 8*a*, 8*b*, 8*c* and 8*d* comprise a presentation error: The guide rod 92 and its bearing members 92*a* and 92*b* for guiding the offset carriage 70 in the x direction should correctly be shown shifted to the left such that the guide rod 92 assumes about the position illustrated by the dashed straight line 92'. In FIG. 6 the guiding device 90 is illustrated correctly in respect of the offset carriage 70.

The mechanism of traversing for the stepwise positioning of the first and second parts of the positioning device 50 becomes clear by way of the FIGS. 8*a*, 8*b*, 8*c* and 8*d*. In these figures part of the receiving plate 52 has been left out to allow a view of the coupling device mechanism beneath. As the offset carriage 70 travels from the position in FIG. 8*c* in the direction of the negative x axis ("to the right") to the position in FIG. 8*d*, the pawl member 71 flips away. The tension of the spring member 75 is selected weak enough such that in this movement to the right the offset carriage 70 will not be offset along the y axis. The operation movement generates the coupling movement K by way of shifting the offset carriage 70 from the position shown in FIG. 8*a* to the position shown in FIG. 8*c*. In the coupling movement K of the offset carriage in the direction of the positive x axis (in FIG. 3, 4: "to the left") during the coupling movement K a pin 81 glides along the contact area 74 of the engagement portion 73 of the pawl member (see FIG. 8*b*), thus moving the second part 52 (with the in-line arrangement 80 with pins 81) one increment S in the direction of the positive y axis ("forwardly").

The distance of the offset pins is 4.5 mm, for processing the 384 well microtiter plate. For processing 96 well microtiter plates the receiving plate 52 must be shifted by double the pin distance (9.0 mm). A shifting device (78, 78*a*, 79) serves for adjusting increments. The shifting device is arranged at the offset carriage 70. The pawl member 71 is always urged against a first stop 76 by means of a spring member, presently the (weak) torsion spring 75. Given this position of the pawl member, successive coupling movements K cause every second projection member (pin 81) to be pushed out of the in-line arrangement 80.

Generally, the stop area of the shifting device is preferably adjusted such that the angle of rotation a of the pawl member comprises a predetermined position relative to the direction of the coupling movement K, in particular relative to the x direction corresponding to the desired increment S. Wherein: $S = L \cdot \sin \alpha$, with L being the length of the engagement portion 73 (stem section 73) of the pawl member 71 which in particular substantially corresponds to the length of the contact area 74 (see FIG. 7). Furthermore it should preferably be taken into account that the increment S either corresponds to precisely one distance between pairs of projection members 81 of the in-line arrangement 80, or corresponds to the sum of the distances between two or several projection members or, in particular in the case of an equidistant arrangement of the projection members, corresponds to the integer multiple of the constant distance of the projection members. Preferably the distance of the projection members is selected the smallest possible to allow the highest resolution of increments.

For changing the increment in FIG. 6 or 7 from S=9.0 mm to S=4.5 mm, a second stopper 77 can be placed in front of the first by means of the shifting device. A contact piece 78 is displaceable on the x axis at a guide rod 78*a* which is fastened to the top surface of the offset carriage 70. The contact piece 78 is moved via a shift lever 79 that is pivotally supported at the offset carriage 70 in front of the pawl member 71. Now the pawl member displaces each of the pins 81, no longer every second one only. The associated shift lever 79 is shifted via a shift pin (not shown) at the adapter plates, either shifted by the user or automatically in dependence on the kind of the adapter plate employed. To prevent the contact piece 78 from being unintentionally shifted by the carriage movement of the offset carriage 70, it is preferably retained in position by magnets.

The offset carriage 70 is guided on the guide rods 91, 92 via two ball bushings (see FIG. 7). This allows a very low-friction guide such that the carriage does not cant. It is moved back and forth via two control cables 93, 94 between the positions on the right and the left (see FIG. 6). The control cable 93 on the left is biased by means of a spring 95. Due to the biasing the pins 81 are retained in a pin lock 96, 97 so as to prevent the second part from moving in the y direction in the relative positions spaced apart therefrom by the increment S=4.5 mm or a multiple thereof. The control cable 94 on the right serves for coupling with the pipette guide and the operation movement B. The control cable 94 on the right is the third coupling means of the coupling device. It serves as a transmission member for transmitting the operation movement B to the coupling movement K, which is easily accomplished in particular by means of at least one pulley for the control cable 94. At the tensioning block 98 the control cable 94 is pulled into a spiral wire hose 99 and guided to the coupling.

In FIG. 9 a laboratory apparatus 100 is shown for stepwise distribution of fluid samples to different sample container elements, in particular for stepwise distribution to different second parts. The laboratory apparatus comprises a base member 101 at which two lateral beams 102 are fastened as a rack, carrying a cross beam 103 from which the first part 51 is suspended. The first part 51 is arranged at this cross beam 103 substantially immovably in the y direction and is arranged at this cross beam 103 substantially movably in the x-z plane.

Figure 4:
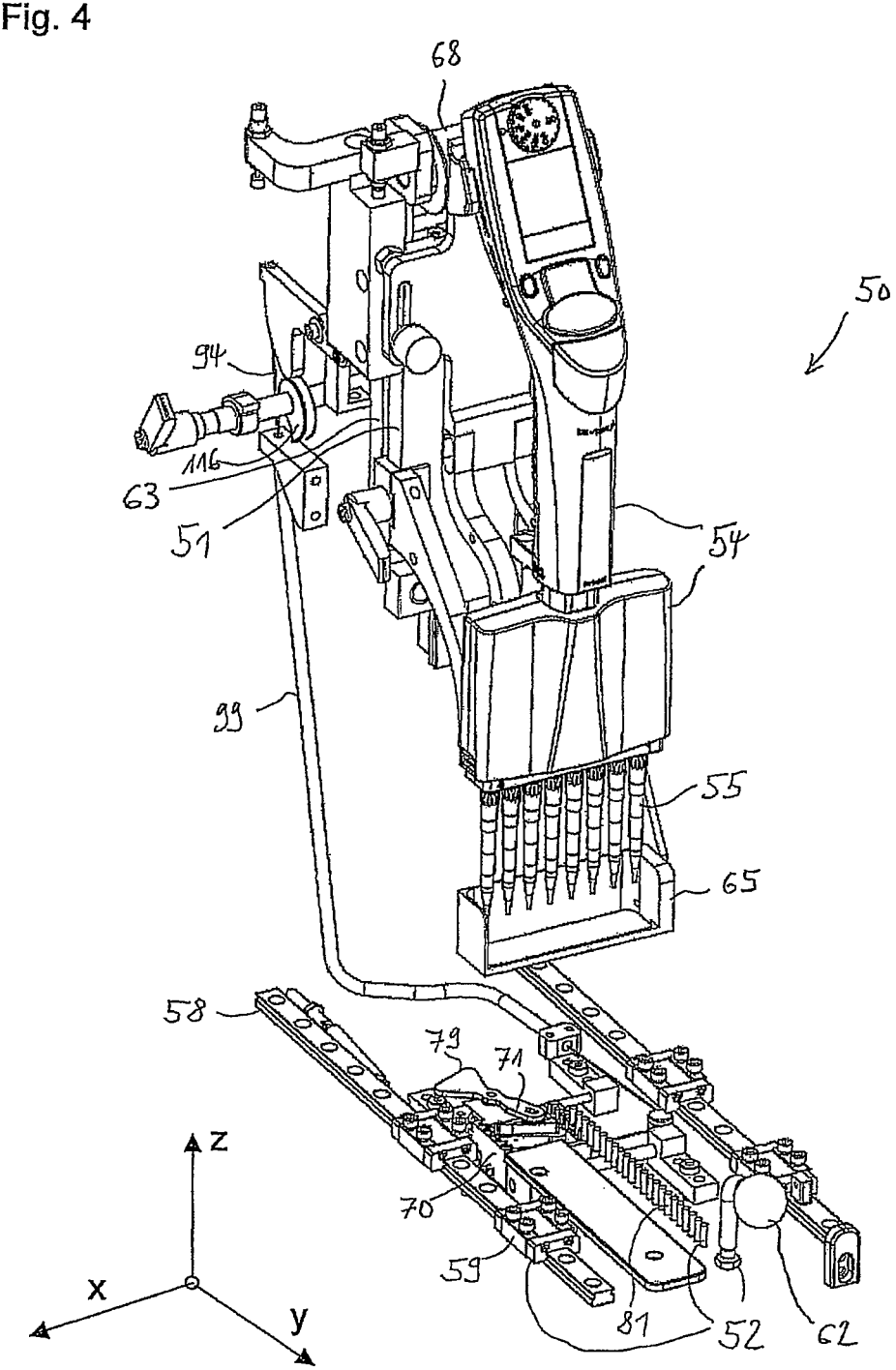
FIG. 4 shows the positioning device of FIG. 3, comprising transport device, without receiving plate, without sample container holder and without microtiter plate.

The first part 51 movable by means of the operation movement B is shown in the FIGS. 3 and 4 with four other assemblies namely, the x carriage, the z carriage 51, the holding device for the transport device (pipette holder) and a swing-in container device 65. Each of the assemblies has at least one function in respect of the positioning device or in respect of the function of the laboratory apparatus.

The x carriage allows the pipette movement in the x direction for positioning the first part 51 with the pipette 54 relative to multiple second parts along the x axis and for using together with these for the distribution of samples (see FIG. 9). To this end the x carriage 63 is supported via a linear guide 64 to the cross beam 103 (see FIG. 9). Moreover the x carriage itself may be connected with the z carriage via a linear guide to be components of the height adjusting device together with it. Moreover it is preferably connected with a guide for the swing-in container device 65, in particular with a linear guide. The container device 65 may e.g. be used as a droplet collector. By means of the linear guide this droplet collector can be moved due to the movement of the z carriage 51 out of the guide track of the pipette if the user moves it downwardly during the operation movement. The container device 65 may be set up as a manual (or automatic) swing-in container device which can be manually swung by the user into the guide track of the pipette along the operation movement. This container device may be set up as a supply container for providing the fluid sample such that the user is not required to change the x position to once again fill pipette tips 55. For filling the pipette tip the sample to be distributed is usually removed from another sample container arrangement which may be arranged on another second part 52a, 52b, 52c (see FIG. 9).

The z carriage 51 is the connecting link to the pipette holder. The pipette holder 67 is connected with the z carriage 51 via a clamping mechanism allowing a height adjusting device 68 for adjusting the height of the pipette holder. The clamping mechanism consists of two prism blocks 66 which are pressed against the z carriage (see FIGS. 3, 4). To this end the prism blocks are drawn together by means of a drawing shaft via the clamping lever 66'. For the automatic, vertical return of the z carriage 51 to its initial height (starting position) it is connected with the x carriage 63 via a spring member 68 namely, a return spring 68. The coil spring 68 employed therefore can be unwound from the spring roll 68' at a constant force, thus generating an even load. Such a spring arrangement is particularly reliable and comfortable in handling to the user.

The pipette holder 67 fixates the pipette via the holding tray 67' and the pipette hook 67". The holder 67 can be rotated via an inclining device 69 with a hinge pin (not visible) at the bottom end of the supporting arms 69" for the tips 55 to be guided to the inner wall of the sample containers 67 of a microtiter plate 66. The inclination angle can be set via a tilt adjusting screw 69'. To prevent the pipette from tilting unintentionally it is automatically pulled back to the starting position by a pair of springs (not visible).

Pipette guide: x and z carriage allow free movement of the first part with the pipette in the x-z plane. It is preferred, however, for the pipette to be adapted to be positioned more precisely relative to the second parts 52, 52a, 52b and 52c. For this reason the first part 51 is guided by a guide track 104 (see FIG. 9). To this end the z carriage 51 is provided with a guide pin 51a (see FIGS. 3, 4, 9). The guide track 104 allows a guided x-z movement at every second part 52, 52a, 52b, 52c. In the case of an x-z movement the guide pin 51a glides into a positioning hopper 104a which downwardly prevents the first part from moving further in the x direction. In this way the positioning of the pipette can be very accurately predetermined relative to the second parts in the x and in the z directions. Limiting the z movement of the pipette receiver is controlled by way of the adjustable depth stops 105 (see FIG. 9) onto which a depth stop damper 51b is guided.

Coupling of offset mechanism and operation movement: The first part 51 (z guide) is coupled with the offset mechanism of the coupling device via a control cable 94. For triggering the offset mechanism and causing transmitting of the operation movement to the positioning movement the control cable 94 must be pulled somewhat out of the spiral wire hose 99. To this end the control cable 94 is coupled with the z carriage 51 via a switch rocker 110. By way of a vertical movement of the z carriage 51 the switch rocker 110, 110a of the respective second part 52, 52a is pivoted about the rocker axis 111, 111a. Thus the movement of the control cable triggers the offset mechanism. Following rotation of the switch rocker 110 about a defined angle, the bearings 112 (e.g. ball bearings) attached to the front rocker face glide along the z carriage 51. In this way exactly the required deflection of the offset carriage is generated.

Unlocking the second parts (FIGS. 3, 4, 9): To allow free displacement of all of the second parts 52, 52a, 52b, 52c in the y direction it is presently provided for them to be unlocked first. To this end the switch rockers 110, 110a, 110b, 1110c of all of the modules are deflected by a defined angle via an eccentric shaft 115. The shaft 115 on which the eccenters 116 are arranged is rotated via the unlocking levers 117. The required angle of rotation is preset. This slight deflection causes the offset carriage 70 to be moved just sufficiently for the offset pins 81 to be no longer secured by the pin lock 96, 97 (see FIGS. 6, 7). In this way the offset pins 81 can be moved through between the pin lock 96, 97 and the pawl member 71 and thus the second parts can be displaced.

Preferably every possible operational step is intended to be carried out on each of the second parts 52, 52a, 52b, 52c as well. This is why adapter devices 121, 122, 123, 124 are provided to be fastened to the receiving plate 52 and to receive another container each. An adapter device may for example be provided to receive a sterile box for providing tips, a 96 well microtiter plate, a 384 well microtiter plate, a 96 deep well plate, a liquid container, and a used tips container. The unambiguous positioning of the microtiter plates in an adapter 123 is obtained by way of a spring 125 (see FIG. 9).

This spring urges the microtiter plate 56 against positioning pins 126, so as to keep the microtiter plate 56 from slipping even as the second part 52b is offset. The adapters are likewise ultimately positioned and fixated on the receiving plate 52 via positioning pins 127 (see FIG. 5). To prohibit the adapter plates 121, 122, 123, 124 from inadvertently slipping off the receiving plate 52, these are secured and can only be lifted off the receiving plate 52 in a specific position of the second part 52. For automatic selection of the correct offset distance S the adapter plates 121, 122, 123, 124 may have fastened to them the shift pins described above for switching the shifting device. Thus, by way of inserting the adapter 121, 122, 123, 124, a shift pin (not visible) can automatically convey the shift lever 79 of the offset carriage 70 to the correct position. In this way the offset distance S does not need to be adjusted by the operator. As an alternative, however, this would be likewise possible. What would be likewise possible would be a program-controlled or electronic switching for setting the increment desired.

The sequence of movements of the positioning device according to the invention and the laboratory apparatus according to the invention allow a precise, simple, and ergonomically comfortable movement of the hand pipette for automatic stepwise displacement in respect of the sample containers. By way of one, several, or all of the preferably provided and described structural measures it is preferably achieved that the pipette guide can be operated one-handedly, that the pipette tips are guided into the sample containers contactless, that after each pipetting cycle a change of positioning is triggered, selectively by 9 mm or by 4.5 mm, that the ingoing depth of the pipette tip into the sample containers is limited, and that such limitation can be adapted, that dispensing of liquid is possible at the inner wall of the sample containers, that receiving and dispensing of tips occurs without any complications, and that the multidispenser function is provided. All of this may be implemented by way of the positioning device and laboratory apparatus which are realized purely mechanically in the exemplary embodiment.

The invention claimed is:

1. Laboratory apparatus for the distribution of fluid samples comprising at least one positioning device,
the positioning device comprising:
a base member,
a first part, which comprises a holding device for holding a transport device for transporting the fluid samples to a target position at which the fluid samples are dispensed from the transport device to the at least one sample container element, the first part being arranged at the base member for carrying out at least one operation movement,
a second part comprising a sample container holder, which is set up to hold the at least one sample container element, the second part being arranged at the base member,
the first part and the second part being arranged movable relative to one another for carrying out at least one positioning movement and adapted to be arranged in relative positions,
a coupling device for coupling the operation movement and the positioning movement,
the coupling device being configured such that the relative positions of the first part and second part can be stepwise changed by way of repeating the operation movement, one operation movement moving the first and second parts starting out from an n-th relative position to the (n+1)th relative position and another operation movement moving the first and the second part starting out from the (n+1)th relative position to the (n+2)th relative position;
wherein the coupling device comprises at least one mechanically acting coupling means for coupling the operation movement and the positioning movement to cause stepwise changes to the relative position;
characterized in that
the second part is arranged to be movable relative to the base member and that the at least one coupling means comprises at least one first coupling means arranged to be movable relative to the sample container holder by means of the operation movement, and comprises at least one second coupling means which is arranged to be immovable relative to the sample container holder, and wherein the coupling device is set up such that the operation movement causes a coupling movement of the at least one first coupling means and that said coupling movement mechanically interacts with the second coupling means for changing the relative position by one step of a predetermined increment.

2. The laboratory apparatus according to claim 1, characterized in that the at least one coupling means comprises a pawl member which is preferably arranged for transfer of the operation movement of the first part to the positioning movement of the second part.

3. The laboratory apparatus according to claim 1, characterized in that the at least one first coupling means comprises a carriage member movable relative to the at least one second coupling means and a guiding device by means of which the carriage member can perform a directed coupling movement with the direction of said coupling movement preferably running substantially linearly and perpendicularly to the positioning movement.

4. The laboratory apparatus according to claim 1, characterized in that the coupling device comprises a third coupling means which is a control cable member acting as a transfer member, by means of which the operation movement is transferred to a coupling movement.

5. Laboratory apparatus for the distribution of fluid samples comprising at least one positioning device,
the positioning device comprising:
a base member,
a first part, which comprises a holding device for holding a transport device for transporting the fluid samples to a target position at which the fluid samples are dispensed from the transport device to the at least one sample container element, the first part being arranged at the base member for carrying out at least one operation movement,
a second part comprising a sample container holder, which is set up to hold the at least one sample container element, the second part being arranged at the base member,
the first part and the second part being arranged movable relative to one another for carrying out at least one positioning movement and adapted to be arranged in relative positions,
a coupling device for coupling the operation movement and the positioning movement,
the coupling device being configured such that the relative positions of the first part and second part can be stepwise changed by way of repeating the operation movement, one operation movement moving the first and second parts starting out from an n-th relative position to the (n+1)th relative position and another operation movement moving the first and the second part starting out from the (n+1)th relative position to the (n+2)th relative position, wherein the coupling device comprises at least one mechanically acting coupling means for coupling the operation movement and the positioning movement to cause stepwise changes to the relative position;

characterized in that the second part is arranged to be immovable relative to the base member and that the at least one coupling means comprises at least one first coupling means arranged to be movable relative to the sample container holder by means of the operation movement, and comprises at least one second coupling means which is arranged to be immovable relative to the first part, and wherein the coupling device is set up such that the operation movement causes a coupling movement of the at least one first coupling means and that said coupling movement mechanically interacts with the second coupling means for changing the relative position by one step of a predetermined increment.

6. The laboratory apparatus according to claim 1 or 5, characterized in that the at least one second coupling means comprises a tooth rack member or an in-line arrangement of projection members.

\* \* \* \* \*